United States Patent [19]

Knaak

[11] 3,978,145

[45] Aug. 31, 1976

[54] USE OF HEXAGONAL CHROMIUM (111) OXIDE HYDROXIDE CATALYST IN FLUORINATION PROCESS

[75] Inventor: Joachim F. Knaak, Wilmington, Del.

[73] Assignee: E. I. Du Pont de Nemours and Company, Wilmington, Del.

[22] Filed: Nov. 14, 1974

[21] Appl. No.: 523,710

[52] U.S. Cl............................ 260/653.6; 260/465.7; 260/544 F; 260/544 Y; 260/593 H; 260/601 H; 260/653.7
[51] Int. Cl.$^2$.................. C07C 17/08; C07C 17/20
[58] Field of Search.......... 260/653.7, 465.7, 544 F, 260/544 Y, 593 H, 601 H, 653.6

[56] References Cited

UNITED STATES PATENTS

| 3,413,363 | 11/1968 | Pindzola | 260/653.7 |
| 3,755,477 | 8/1973 | Firth et al. | 260/653.7 |

Primary Examiner—D. Horwitz

[57] ABSTRACT

An improved process for the reaction of halogenated aliphatic compounds with HF using hexagonal —CrOOH as the catalyst to produce fluorine containing aliphatic compounds.

5 Claims, No Drawings

USE OF HEXAGONAL CHROMIUM (111) OXIDE HYDROXIDE CATALYST IN FLUORINATION PROCESS

BACKGROUND OF THE INVENTION

The vapor phase reaction with hydrogen fluoride has long been used for the fluorination of aliphatic compounds containing halogens other than fluorine particularly chlorine and bromine. Chromium (III) oxide catalysts have been used for reactions of this type. Chromium (III) oxides used for this reaction have been obtained by reduction of chromium (VI) oxide $CrO_3$ with ethanol, by dehydration of the commercial pigment "Guignet's Green", and by precipitation of a water-containing chromium (III) trihydroxide by treating aqueous solutions of chromium (III) nitrate or other water-soluble salts with an alkaline reagent. Although chromium (III) oxides so obtained have long been considered to be amorphous, it has recently been found by a combination of X-ray and electron diffraction analysis that these oxides do have a crystal structure and that the chromium (III) oxides so prepared exhibit a $\gamma$-CrOOH orthorhombic crystallinity.

While the fluorination processes previously known provided a satisfactory means of replacing halogens with fluorine a continuing need exists for processes which operate effectively with a reduced need for catalyst replacement.

SUMMARY OF THE INVENTION

The present invention provides a fluorination process involving a catalyst which retains its effectiveness in the process over longer periods of time than have heretofore been possible.

Specifically, there is provided in the vapor phase reaction of a halogenated aliphatic compound containing halogen atoms other than fluorine with HF over a chromium (III) oxide catalyst at a temperature of about from 150° to 700°C. to produce halogenated aliphatic compounds containing increased numbers of fluorine atoms, the improvement wherein the catalyst is hexagonal chromium (III) oxide hydroxide.

DETAILED DESCRIPTION OF THE INVENTION

The halogenated aliphatic starting materials used in the present process are aliphatic compounds containing at least one halogen atom other than fluorine in the molecule which can be replaced by fluorine by reaction with HF. These include both halogenated aliphatic hydrocarbons and halogenated aliphatic compounds containing functional groups. The compounds can contain from one to eight carbons in which adjacent carbon atoms are linked by 1 or 2 valence bonds and include halogenated alkanes, halogenated cycloalkanes, halogenated alkenes and halogenated cycloalkenes. The halogens can be fluorine, bromine or chlorine with at least one chlorine or bromine. Typical compounds are shown in Swamer et al., U.S. Pat. No. 3,258,500 hereby incorporated by reference.

Compounds that can be fluorinated according to the present process and which have functional groups include perhaloacetones of the formula $CX_3COCX_3$, perhaloacetyl halides of the formula $CX_3COX$, perhaloacetonitriles of the formula $CX_3CN$ and trihaloacetaldehydes of the formula $CX_3CHO$ wherein X is chlorine or fluorine, at least one X being chlorine.

The halogenated aliphatic hydrocarbons can be preformed or formed in situ. For in situ formation, mixtures of aliphatic hydrocarbons such as methane, ethane, ethylene or acetylene, and chlorine can be combined with the HF in the manner shown by Vecchio et al. in U.S. Pat. Nos. 3,294,852 and 3,442,962.

The catalyst used in the present process is hexagonal chromium (III) oxide hydroxide. This material is described in detail in Douglas, Acta Crystallographica, 10, 423 (1957), hereby incorporated by reference, and is commonly referred to as $HCrO_2$. Reference to this material herein will be made as "hexagonal —CrOOH."

The hexagonal —CrOOH catalyst can be prepared in bulk form by heating $\gamma$-CrOOH with water in a pressure vessel under autogenous pressure at elevated temperatures, for example at about from 250° to 280°C. for 24–48 hours. After heating, the vessel is cooled and the catalyst material recovered. Any source of $\gamma$-CrOOH which is substantially free of small ions such as alkali metal ions can be used, including, for example, $\gamma$-CrOOH "gel catalyst" and $\gamma$-CrOOH COT catalyst. "Guignet's Green" pigment, for example, is unsuitable for preparing hexagonal —CrOOH because it usually contains such small ions.

Hexagonal —CrOOH catalyst can also be prepared on inert supports such as carbon or alumina. Calcium fluoride supports are particularly satisfactory. The supported catalysts can be prepared by first preparing $\gamma$-CrOOH on the support by mixing the support with chromium trioxide ($CrO_3$) solution and reducing with ethanol. The catalysts can also be made by slurring the support with a solution of chromium (III) nitrate and adding ammonium hydroxide to precipitate the chromium (III) hydroxide. In either case, the $\gamma$-CrOOH on support is heated with water under autogenous pressure to convert it to the hexagonal —CrOOH, as described for the bulk material. X-ray and electron diffraction studies show the catalyst to retain its hexagonal —CrOOH configuration on the support. Calcium fluoride is a preferred support because it tends to further increase the catalyst life. Certain other fluorides such as barium fluoride, strontium fluoride or zinc fluoride should be avoided as supports since they tend to poison the catalyst.

The catalyst can be used in any form which is convenient to the reaction system in use. Generally for larger scale operations the catalyst will be used in the form of pellets or like shapes which are made in the usual manner. Pellets having increased strength to withstand fracture in use can be prepared by including about 15% by weight Sorel's cement in the catalyst. Sorel's cement is a magnesium oxychloride formed in situ by including with the catalyst magnesium oxide and magnesium chloride in a molar ratio of about 4.7 to 1. Inclusion of Sorel's cement in the hexagonal —CrOOH catalyst has not been found to alter the activity of the catalyst.

The hexagonal —CrOOH catalysts are preferably preactivated by heating in an inert gas, by the techniques described in Swamer et al., U.S. Pat. No. 3,258,500. Such activation is particularly advantageous for large scale reactions. Activation can also occur during the reaction of HF with halogenated aliphatic compounds if the reaction temperature is above about 300°C. For lower reaction temperatures prior activation of the catalyst is needed for satisfactory performance of the process.

Conditions for the reaction of HF with halogenated aliphatic compounds will to some extent depend on the nature of the starting materials and products desired. In general, reaction temperatures of from 150° to 700°C can be useful in fluorinating halogenated aliphatic hydrocarbons. When reacting perhaloketones, acid halides, nitriles or aldehydes, the maximum temperature used should be about 550°C., to prevent thermal degradation of the products.

The molar ratio of HF to halogenated aliphatic compound will, in general, be at least one mole of HF per mole of halogen to be replaced. Usually an excess of HF is used, particularly where it is desired to replace all halogens other than fluorine. When incomplete replacement of halogen is desired, the molar ratio of HF to replaceable halogen should be near that desired to replace the desired number of halogens.

The pressures at which the present reaction are carried out are not critical, and atmospheric pressure is preferred for convenient operation.

It has surprisingly been found that when $\gamma$-CrOOH catalysts are replaced by hexagonal —CrOOH for the vapor phase reaction of halogenated aliphatic compounds with HF, the useful catalyst life is increased up to several times without any significant change in activity. The hexagonal —CrOOH catalyst has been found to have at least about the same activity as the $\gamma$-CrOOH catalyst. Under otherwise identical conditions $\gamma$-CrOOH and hexagonal —CrOOH have at least about the same productivity in terms of grams product/gram catalyst/hour. Hexagonal-CrOOH also has substantially the same facility as $\gamma$-CrOOH for halogen replacement as well.

The following examples further illustrate the present invention.

EXAMPLE 1

To prepare hexagonal —CrOOH catalyst, 25 parts of $\gamma$-CrOOH "gel catalyst" is charged into a pressure vessel having a capacity of 250 parts water. 50 parts water are added, the vessel is sealed and heated to 250°C. for 20 hours. The vessel is cooled to ambient temperature with an air stream, the vessel opened and blue-green solids are recovered.

To prepare the catalyst on a calcium fluoride support, a mixture of 600 parts water and 40.8 parts calcium fluoride powder is first slurried in a reaction vessel equipped with agitation and a reflux condenser. Then 48 parts of chromium trioxide ($CrO_3$) is added and stirred until dissolved, followed by the addition of 29 parts 95% ethanol in small increments at 5 minute intervals. After agitating for three hours, a further 29 parts 95% ethanol is added in increments as before. The mixture is then heated under reflux for 16 hours. The mixture is then cooled and the solids collected by filtration, air being passed through the solids until the cake cracks into small pieces. The solids are then dried under vacuum for 24 hours at 60° to 70°C.

A mixture of 50 parts of the above solids and 50 parts water is placed in a pressure vessel of 250 parts water capacity. The vessel is sealed and heated at 280°C. for 48 hours. After cooling to ambient temperature, the vessel is opened and the solids recovered. X-ray diffraction analysis demonstrates the presence of hexagonal —CrOOH and $CaF_2$ as separate crystalline species in the solid.

Supported and unsupported catalysts prepared as described above were used in a fluorination process. The apparatus used consisted of a 1.905 cm diameter by 30.48 cm long Inconel tube vertically mounted in a constant temperature salt bath and having a thermocouple mounted in the center of the tube to measure catalyst bed temperature. Refrigerant grade dichlorodifluoromethane from a commercial cylinder was fed via a standpipe through a cylinder containing liquid HF held in a constant temperature bath at 4° ± 0.2°C., so as to provide a constant mole ratio of HF to $CF_2Cl_2$ of 4/1. The $CF_2Cl_2$/HF mixture was fed to the bottom of the reactor. Products leaving the reactor were passed through 20% aqueous sodium hydroxide to remove acids, drying agents and then a wet test meter to measure volume of products as a function of time. Samples of the product stream after removal of acids were periodically taken for vapor phase chromatographic analysis.

In all tests the following conditions prevailed:
catalyst weight: 2g — 12/20 mesh flow rate $CF_2Cl_2$: 10g/g catalyst/hr.
reactant ratio HF/$CF_2Cl_2$: 4/1
reactor temperature: 400°C.

The useful catalyst life was considered to be reduced when 1 volume % of unreacted $CF_2Cl_2$ was found in the product.

The reaction was repeated, using two types of $\gamma$-CrOOH as the catalyst instead of the hexagonal —CrOOH. $\gamma$-CrOOH "Gel Catalyst" was prepared by a procedure identical to that described by Swamer et al., U.S. Pat. No. 3,258,500, Example 1A, except that the filter cake was dried at 60°-70°C. for 24 hours and not further activated. $\gamma$-CrOOH "COT" catalyst was prepared by the process of Swamer et al., U.S. Pat. No. 3,258,500, Example 9, first paragraph.

The results with the hexagonal —CrOOH catalysts of this invention were compared with the $\gamma$-CrOOH catalysts of the art in Table 1 below.

TABLE 1

| Catalyst | Activity* (400°C.) | Catalyst Life (Hrs.) |
|---|---|---|
| Hexagonal - CrOOH | 70–40 | 550 |
| Hexagonal - CrOOH on $CaF_2$ | 70–40 | 750 |
| $\gamma$-CrOOH - "Gel Catalyst" | 75–40 | 30 |
| $\gamma$-CrOOH - "COT Catalyst" | 70–50 | 100 |

*Volume % $CF_4$ in product over life of catalyst

EXAMPLE 2: Reaction of Vinyl Chloride and HF

Vinyl chloride and HF were reacted over hexagonal —CrOOH catalyst using the same apparatus and procedure as in Example 1, except that the vinyl chloride and HF were maintained as separate gas streams until just prior to entering the reactor. The temperature used was about 250°C., the HF/vinyl chloride mole feed ratio was 3.5/1, the space velocity was 118/hr. The major product was 1,1-difluoroethane with minor amounts of vinyl fluoride, 1-chloro-1-fluoroethane and 1,1-dichloroethane and trace amount of ethylene, acetylene and others. A 1,1-difluoroethane yield of 95.8% and vinyl chloride conversion of 57% were obtained at 250°C., a HF/vinyl chloride ratio of 3.5/1 and a space velocity of 118/hr.

EXAMPLE 3

The procedure for Example 1 was repeated, except that hexachloroacetone was used in place of dichlorodifluoromethane. Because hexahaloacetones react with both alkali and water, the apparatus was modified so that gas samples were withdrawn prior to contact with the aqueous alkali. The gas stream was passed through absorbers containing sodium fluoride to remove both HCl and HF, then collected for analysis. The following conditions prevailed:

| | |
|---|---|
| catalyst weight: | 35 g. |
| flow rate: | 0.7 g/g catalyst/hr. |
| reactant ratio HF/CCl$_3$COCCl$_3$: | 14.1 |
| Reactor temperature: | 375–380°C. |

The end of useful catalyst life was considered to be the appearance of less than 65% by volume of hexafluoroacetone in the product. The process was repeated using γ-CrOOH ("COT catalyst") and a comparison of the result is summarized in Table 2 below.

TABLE 2

| Catalyst | Activity* (375°C.) | Life (hours) |
|---|---|---|
| hexagonal - CrOOH | 90–65 | 750 hrs. |
| γ-CrOOH ("COT" catalyst | 93–65 | 400 hrs. |

*Volume % hexafluoroacetone in product over life of catalyst.

I claim:

1. In the vapor phase reaction of a halogenated aliphatic compound containing halogen atoms other than fluorine, the compound containing from 1 to 8 carbon atoms in which adjacent carbon atoms are linked by one or two valence bonds and the compound being selected from halogenated aliphatic hydrocarbons, perhaloacetones, perhaloacetyl halides, perhaloacetonitriles and trihaloacetaldehydes, the compound being reacted with HF over a chromium (III) oxide catalyst at a temperature of about from 150° to 700°C. to produce halogenated aliphatic compounds containing increased numbers of fluorine atoms, the improvement wherein the catalyst is hexagonal chromium (III) oxide hydroxide.

2. A process of claim 1 wherein the hexagonal chromium (III) oxide hydroxide is present on an inert support.

3. A process of claim 1 wherein the catalyst is present in the form of pellets and further comprises magnesium oxychloride binder.

4. A process of claim 1 wherein the halogenated aliphatic compound is a halogenated aliphatic hydrocarbon.

5. A process of claim 4 wherein the hydrocarbon is halogenated with chlorine and fluorine atoms.

* * * * *